(12) United States Patent
Amelia et al.

(10) Patent No.: US 8,111,806 B2
(45) Date of Patent: Feb. 7, 2012

(54) CHARGED PARTICLE BEAM THERAPY SYSTEM HAVING AN X-RAY IMAGING DEVICE

(75) Inventors: Jean-Claude Amelia, Erquelinnes (BE); Frederic Genin, Ottignies (BE)

(73) Assignee: Ion Beam Applications, Louvain-Neuve (BE)

( * ) Notice: Subject to any disclaimer, the term of this patent is extended or adjusted under 35 U.S.C. 154(b) by 149 days.

(21) Appl. No.: 12/755,096

(22) Filed: Apr. 6, 2010

(65) Prior Publication Data

US 2010/0272241 A1 Oct. 28, 2010

(30) Foreign Application Priority Data

Apr. 22, 2009 (EP) .................................... 09158502

(51) Int. Cl.
*G01N 23/04* (2006.01)
(52) U.S. Cl. .......................................... 378/63; 378/143
(58) Field of Classification Search .................... 378/63, 378/65, 143, 119, 123, 125, 138
See application file for complete search history.

(56) References Cited

U.S. PATENT DOCUMENTS

| | | |
|---|---|---|
| 5,117,829 A | 6/1992 | Miller et al. |
| 5,471,516 A * | 11/1995 | Nunan ............................. 378/65 |
| 6,445,766 B1 * | 9/2002 | Whitham .......................... 378/65 |
| 7,831,021 B1 * | 11/2010 | Schumacher et al. ........ 378/143 |
| 2010/0310045 A1 * | 12/2010 | Brown et al. .................... 378/62 |

FOREIGN PATENT DOCUMENTS

| | | |
|---|---|---|
| EP | 1454653 | 9/2004 |
| WO | 98/18523 | 5/1998 |
| WO | 2005/018734 A2 | 3/2005 |
| WO | 2007/060242 A1 | 5/2007 |

* cited by examiner

*Primary Examiner* — Hoon Song
(74) *Attorney, Agent, or Firm* — Norris, McLaughlin & Marcus, PA; Christa Hildebrand, Esq.

(57) ABSTRACT

Therapy system (100) for irradiating a target volume (2) of a patient (1) with a charged particle beam (6), including a beam generator (3), a beam transport system (4), and a nozzle (5) for distributing the beam to the target volume (2), the nozzle (5) being, when in operation, under vacuum. The therapy system comprises an X-ray device (10) which is rotatably mounted inside the nozzle (5) between a first position and a second position. In the first position, an X-Ray source (12) within the X-Ray device is able to emit X-Rays along a charged particle beam path for generating an X-Ray image on a corresponding X-Ray receiving device (11) arranged opposite to the patient (1), said X-Ray image serving to determine a correct position of the target volume (2) with regard to the charged particle beam (6). In the second position, the X-Ray device (10) is set outside of a charged particle beam treatment path envelope (23), so that the charged particle beam (6) can reach and irradiate the target volume (2).

6 Claims, 5 Drawing Sheets

CHARGED PARTICLE BEAM THERAPY SYSTEM HAVING AN X-RAY IMAGING DEVICE

BACKGROUND OF THE INVENTION (1) Field of the Invention

The invention relates to a therapy system for irradiating a target volume within a patient with a charged particle beam, comprising
- a charged particle beam generator,
- a beam transport system for transporting the charged particle beam,
- a nozzle for delivering the charged particle beam to the target volume,
- an X-Ray device comprising an X-Ray source for emitting X-Rays towards the target volume, the X-Ray device being movably mounted into the nozzle between a first position wherein the X-Ray device is inside of a treatment path envelope of the charged particle beam within the nozzle and a second position wherein the X-Ray device is outside of said treatment path envelope,
- an X-Ray receiving device mounted opposite to the patient with regard to the X-Ray source, and in optical alignment with the X-Ray source when the X-Ray device is in the first position, (2) Description of Related Art Such therapy systems are known from international patent application number PCT/US97/19236, published under international publication number WO98/18523.

In such known therapy systems, an X-Ray device including an X-Ray source, for example an X-ray tube, is movably mounted inside the nozzle between aforementioned two positions. When the X-Ray device is in its first position, the X-Ray source is able to emit X-Rays towards the X-Ray receiving device for generating an X-Ray image of the target volume. Given the position and orientation of the X-Ray source within the nozzle, such image is often called a beam-eye view (BEV) image of the target volume. Such image is used to determine if the target volume is correctly aligned with regard to the charged particle beam path and eventually to modify a spatial position of the patient in order to obtain such correct alignment. When the alignment is correct, the X-Ray device is moved away to its second position so as to leave the path free to the charged particle beam for irradiating the target volume. These basic principles are well known in the art and will therefore not be detailed further.

Of interest here is that, in such known therapy systems, the X-Ray device is moveable between aforementioned two positions following a translatory movement within the nozzle. To this end, international patent application number PCT/US97/19236 discloses for example an X-Ray device comprising an X-Ray source which is mounted on a sled which is moveable along two parallel guiding tracks and a screw motor assembly which is operatively connected to the sled for moving the X-Ray device along the guiding tracks between its two positions.

Although such known systems work well, they require a relatively complex and hence expensive mechanical assembly for moving the X-Ray device. They also set a relatively important stroke on the X-Ray device, which in turn requires particular means for bringing electrical power and cooling fluid to the X-Ray device.

Furthermore, for nozzles applying beam scanning methods for obtaining a conformal irradiation of the target volume, such as pencil beam scanning methods, it is desirable that a certain degree of vacuum is created inside the nozzle in order to reduce scattering effects on the particle beam while it travels within the nozzle. This is particularly true for pencil beam scanning methods where small beam spots are required at an isocenter of the system, such as beam spots having a size between 2 mm and 10 mm.

Now, many of the standard mechanical components which are being used for moving the X-Ray device in the known systems are not suited for operating in a vacuum and would therefore have to be redesigned and/or reengineered for operation in such an environment. This would in turn increase the complexity, the costs, and most probably the weight and the bulk of the system.

BRIEF SUMMARY OF THE INVENTION

It is an object of the invention to provide a therapy system which overcomes at least partially the aforementioned problems of the known systems.

To this end, the therapy system according to the invention is characterised in that the therapy system further comprises vacuum means for creating a vacuum within the nozzle so that, in operation, an internal air pressure inside the nozzle is lower than an external air pressure outside the nozzle, and in that the X-Ray device is rotatably mounted into the nozzle between the first and the second position about a rotation axis which may be either inside or outside of the treatment path envelope of the charged particle beam within the nozzle.

With a system according to the invention, the number and the complexity of the mechanical parts required for moving the X-Ray device between its two positions is reduced, which is particularly attractive in a vacuum environment. The bulk of the system is also reduced since only a rotation axle is to be permanently outside of the treatment path envelope of the beam, whereas, as can be seen for example from FIG. 3 of patent publication number WO 98/18523, the complete mechanical device for moving the X-Ray device, including a.o. the two guiding tracks, must be permanently outside of said envelope in the known systems. Furthermore, with a system according to the invention, the displacement of electrical and fluid ducts to the X-Ray device can also be made smaller, thereby putting less strain on said ducts and increasing their durability.

It is a further object of the invention to provide a therapy system in which the X-Ray source and/or the electrical and fluid ducts to the X-Ray source and/or the means for moving the X-Ray device between its two positions, are, on their outside, subject to the external air pressure.

To this end, the therapy system according to the invention is preferably characterised in that the X-Ray device comprises a container inside which the X-Ray source is mounted, said container having a cylindrical neck whose axis is the rotation axis, said cylindrical neck extending in an air-tight manner through a circular opening of the nozzle and emerging at an open side of the neck at least partially outside of the nozzle With such a preferred therapy system, air at the external air pressure can enter into the container through the open side of its neck and hence all parts which are arranged inside of the container, such as the X-Ray source for example, will be at the external air pressure, yet maintaining the vacuum inside the nozzle even when the X-Ray device is rotating about its rotation axis. An additional advantage of such a preferred therapy system is that electrical and fluid ducts can easily be passed from the outside of the nozzle, through the open side of the neck, to the X-Ray source, along a path which is thus completely at the external air pressure. Furthermore, since the axis of the cylindrical neck is the rotation axis, said ducts can for example be arranged along the rotation axis, which further reduces strain on said ducts when the X-Ray device moves between its two positions.

It is yet another object of the invention to provide a therapy system in which the means for rotating the X-Ray device about the rotation axis are, on their outside, subject to the external air pressure.

To this end, the therapy system according to the invention is preferably characterised in that it further comprises driving means for rotating the X-Ray device about the rotation axis, and in that said driving means are at least partially arranged outside of the nozzle.

In addition to the fact that the driving means will thereby be subject to the external air pressure, such a preferred therapy system presents the further advantage that the driving means will be easily accessible for inspection and/or maintenance.

BRIEF DESCRIPTION OF THE SEVERAL VIEWS OF THE DRAWING(S)

These and further aspects of the invention will be explained in greater detail by way of example and with reference to the accompanying drawings in which.

The figures are not drawn to scale. Generally, identical components are denoted by the same reference numerals in the figures.

DETAILED DESCRIPTION OF THE INVENTION

Figure 1:
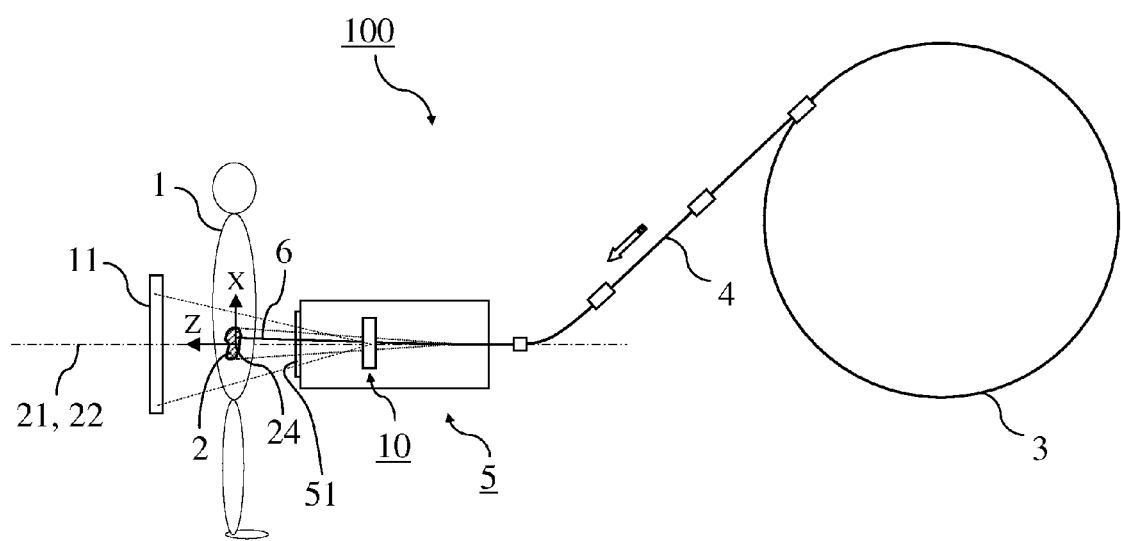
FIG. 1 shows a schematic view of a charged particle beam therapy system according to the invention.

FIG. 1 shows a schematic view of a charged particle beam therapy system 100 according to the invention.

Such therapy system 100 comprises a charged particle beam generator 3 for generating a beam of charged particles, such as protons or carbon ion particles or any other type of charged particle, a beam transport system 4 for transporting the charged particle beam 6 from the generator 3 along a beam path, and a nozzle 5 at an end of such path for delivering the charged particle beam 6 to a target volume 2 within a patient 1. Such a nozzle 5 may apply various target irradiation methods such as beam scattering, beam wobbling, pencil beam scanning, and other methods. The nozzle 5 may be mounted on a gantry for rotation of the nozzle 5 about an isocenter 24 of the system or may be of the fixed beam line type or of any other type.

The nozzle 5 comprises an X-Ray device 10 which includes an X-Ray source 12 for emitting X-Rays towards the target volume 2 so as to substantially form a beam-eye view BEV image of the target volume on an X-Ray receiving device 11 mounted opposite to the patient 1 with regard to the X-Ray source 12. Such image is then used to correctly position the target volume 2 with regard to the charged particle beam 6 before starting irradiation with the charged particle beam 6. The X-Ray source may for example be a commercially available X-Ray tube, or any other type of arrangement for emitting X-Rays.

These and other basic components as well as the operation of such a charged particle beam therapy system are well known in the art and will therefore not be described further.

Figure 2:
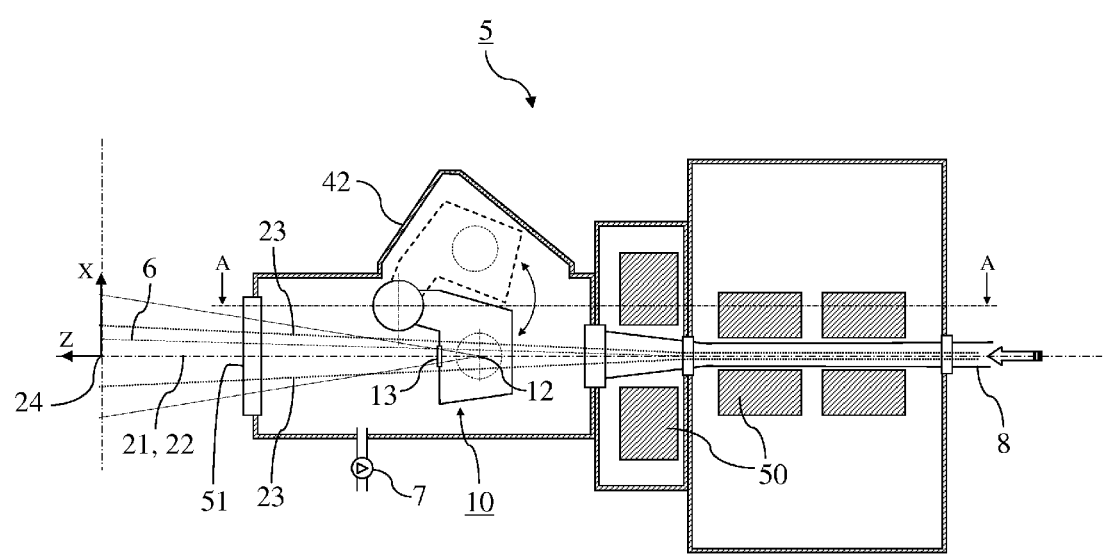
FIG. 2 shows a longitudinal section of the nozzle of the therapy system of FIG. 1.

FIG. 2 schematically shows a longitudinal section of an exemplary embodiment of the nozzle 5 of the therapy system 100 of FIG. 1.

In patient treatment operation, the charged particle beam 6 enters into the nozzle 5 from the right side of the nozzle as seen on the drawing of FIG. 2, propagates through the nozzle 5 wherein the beam is a.o. appropriately shaped and/or deflected, and then exits the nozzle 5 at its left side as seen on the drawing of FIG. 2 towards the target volume 2.

When the beam is not deflected, it follows a nominal path along a central propagation axis 22 of the charged particle beam 6, indicated as the Z axis on FIG. 2.

When the beam is deflected in X and/or Y directions for irradiating the target volume 2, which may for example be achieved with beam scanning magnets 50 in case of pencil beam scanning techniques, it follows—within the nozzle—a set of paths defining a treatment path envelope 23 within the nozzle.

The therapy system further comprises vacuum means 7 for creating a vacuum within the nozzle 5 so that, in operation, an internal air pressure inside the nozzle is lower than an external air pressure outside the nozzle.

Such means may for example comprise a vacuum pump operationally connected upstream in the beam transport system 4 to a beam line 8 through which the charged particle beam travels before entering the nozzle 5, the beam line 8 being in pneumatic connection with the nozzle so that the vacuum is able to propagate through the beam line 8 into the nozzle to create a vacuum inside the nozzle 5. In other terms, air can this way be pumped from the nozzle 5 through the beam line 8.

Preferably, said vacuum means 7 are the same as vacuum means which are used for creating a vacuum inside the beam line for proper propagation of the charged particle beam in said beam line. Alternatively or additionally, the vacuum means 7 may for example comprise a vacuum pump operationally connected to the nozzle 5 as illustrated on FIG. 2.

The term "vacuum" is to be understood as an air pressure which is lower than the external pressure outside of the nozzle 5. Thanks to said vacuum, unwanted scattering of the particle beam within the nozzle 5 is reduced, which yields a narrower beam at the exit of the nozzle. When such means are put into operation, the internal air pressure inside the nozzle 5 may for example drop to 0.01 millibar absolute, or even to 0.001 millibar absolute, whereas the external air pressure outside the nozzle 5 is for example the atmospheric pressure. Preferably, the vacuum means 7 is able to create a vacuum inside the nozzle 5 up to as close as possible to the target volume 2 in the Z direction when the patient 1 is in a treatment position. A beam spot size ranging between 2 mm and 10 mm, measured at the isocenter 24 of the system, can for example be obtained under such conditions.

The X-Ray device 10 is rotatably mounted into the nozzle 5 about a rotation axis 20 between a first position in plain line on FIG. 2 and a second position in dotted line on FIG. 2.

In the present embodiment, the rotation axis 20 is arranged outside of the treatment path envelope 23 of the charged particle beam 6, but it may also be arranged inside of said envelope 23. A rotation axle 25 of the X-Ray device 10 is of course to be arranged outside of said envelope 23 in order not to be in the way of the charged particle beam 6 when the beam follows its treatment paths towards the target volume 2.

The first position corresponds to a rotational position wherein the X-Ray device 10 is at least partially inside of the treatment path envelope 23 of the charged particle beam 6.

The second position corresponds to a rotational position wherein the X-Ray device 10 is completely out of the treatment path envelope 23 of the charged particle beam 6 and wherein the X-Ray source 12 is able to emit X-Rays in the direction of the patient 1.

The X-Ray source 12 defines an optical axis 21, sometimes also called a central ray axis or a reference axis, which is a characteristic feature of the X-Ray source 12. In a preferred embodiment, the first position corresponds to a rotational position of the X-Ray device 10 wherein said optical axis 21 substantially coincides with the central propagation axis 22 of the charged particle beam 6. In another preferred embodiment, the first position corresponds to a rotational position of the X-Ray device 10 wherein said optical axis 21 is substantially parallel to the central propagation axis 22 of the charged particle beam 6.

The therapy system 100 according to the invention further comprises an X-Ray receiving device 11 mounted opposite to the patient 1 with regard to the X-Ray source 12, and in optical alignment with the optical axis 21 of the X-Ray source 12 when the X-Ray device 10 is in the first position. In case the nozzle 5 is mounted on a gantry for rotation of the nozzle about an isocenter 24 of the system, the X-ray receiving device 11 may for example be arranged on the gantry itself in order to preserve the optical alignment when the gantry is rotating.

Hence, when the X-Ray device 10 is in the first position, it is able to generate a beam-eye view image of the target volume 2 on the X-Ray receiving device 11, such image being for example used for correctly positioning the target volume 2 with respect to the charged particle beam 6 before irradiation of said target volume 2 with said beam. When the X-Ray device 10 is in the second position, it stands completely out of the way of the charged particle beam path when said beam is directed to the patient 1 for irradiation treatment of the target volume 2.

As can be seen on FIG. 2, in case of a pencil beam scanning nozzle, the X-Ray device 10 is preferably arranged in the Z direction between beam scanning magnets 50 and a beam exit window 51 through which the charged particle beam 6 exits the nozzle 5 for irradiating the target volume 2. In such a case, the beam scanning magnets 50 may for example be arranged at a Z distance of around 2000 mm from the isocenter 24, the X-Ray device 10 at a Z distance of around 1200 mm from the isocenter 24, and the beam exit window 51 at a Z distance of around 600 mm from the isocenter 24.

Figure 3:
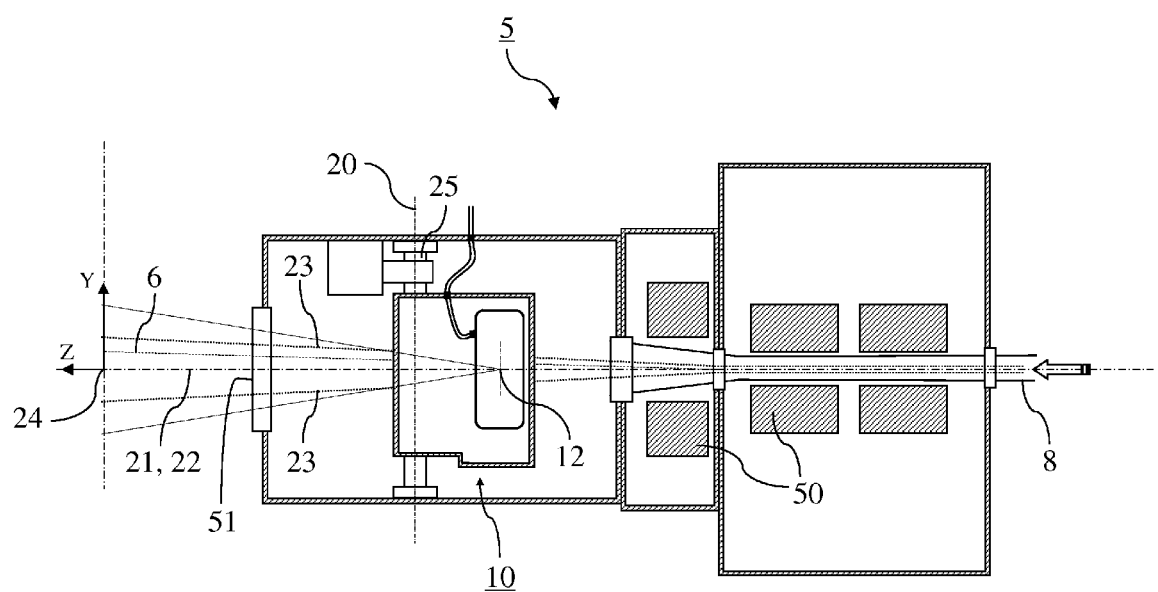
FIG. 3 shows an A-A section of the nozzle of FIG. 2.

FIG. 3 shows an A-A section of the nozzle of FIG. 2. In this view becomes a.o. apparent the Y axis and the treatment path envelope 23 of the charged particle beam 6 within the nozzle 5 in the Y direction.

Figure 4:
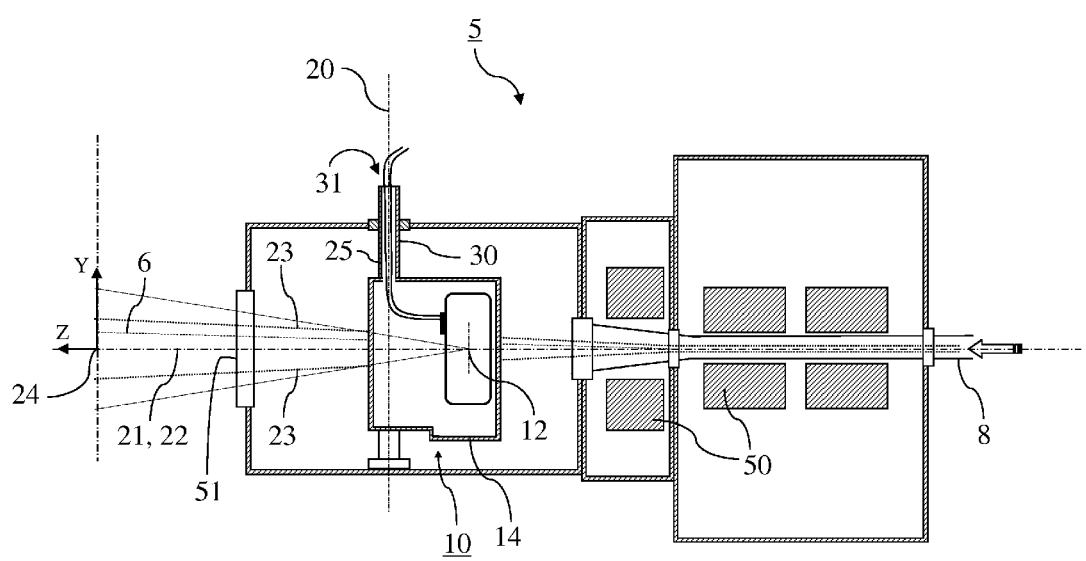
FIG. 4 shows an A-A section of the nozzle of FIG. 2 according to a preferred embodiment of the invention.

FIG. 4 shows an A-A section of the nozzle of FIG. 2 according to a preferred embodiment of the invention.

In such a preferred embodiment, the X-Ray device 10 comprises a container 14 inside which the X-Ray source 12 and possibly other components are arranged.

The container comprises an air-tight aperture 13 through which the X-Ray source 12 can emit X-Rays towards the target volume 2. The dimensions of said aperture 13 are preferentially chosen so as to provide the maximum X-ray field size that is required at the isocenter 24, such as for example an X-ray field of 30 cm×40 cm at the isocenter 24.

The container 14 further presents a cylindrical neck 30 which extends in an airtight manner through a circular opening of the nozzle 5 and which emerges at an open side of the neck 31 at least partially outside of the nozzle 5. Hence, the axis of the cylindrical neck 30 is the axis about which the X-Ray device 10 is able to rotate. A combination of a bearing and a circular joint arranged on the nozzle 5, concentrically with the circular opening, can for example be used to that effect.

Since the open side of the neck 31 emerges outside of the nozzle 5, air at the external pressure can freely enter into the container 14 so that its inside will be at the external air pressure. Any component arranged into said container, such as the X-ray source 12, will therefore be able to operate at the external air pressure, such as the atmospheric pressure.

Preferably, the container 14 also presents an axle at an opposite side of the neck 31 along the same rotation axis 20 as well as a second bearing mounted on the nozzle 5 for cooperation with said axle. Alternatively, said axle is a bearing and said second bearing is an axle.

Figure 5:
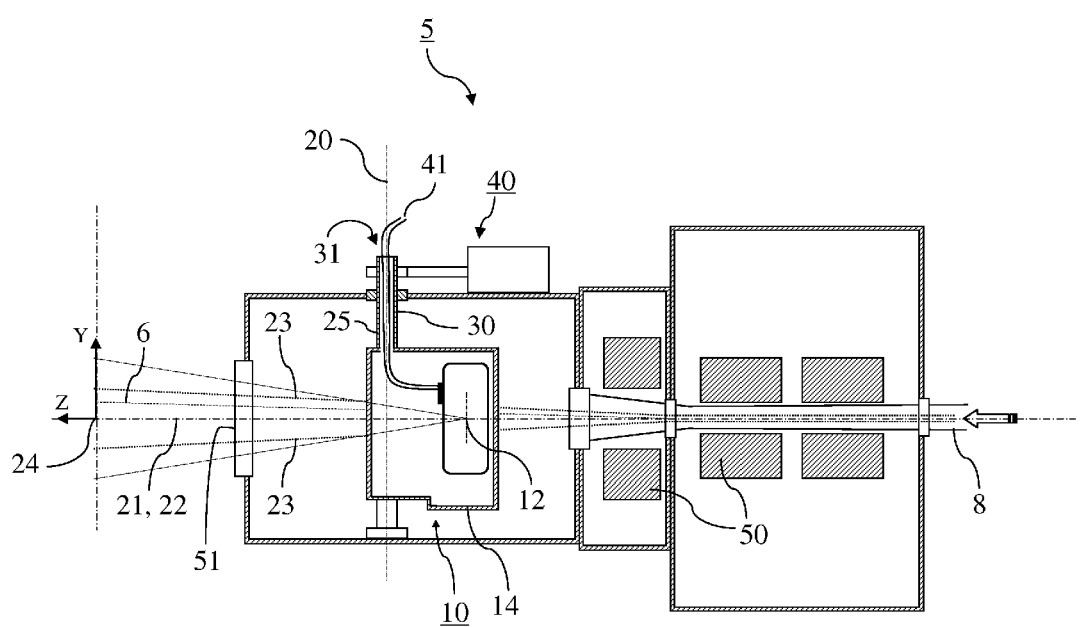
FIG. 5 shows an A-A section of the nozzle of FIG. 2 according to a further preferred embodiment of the invention.

FIG. 5 shows an A-A section of the nozzle of FIG. 2 according to a further preferred embodiment of the invention.

According to such a further preferred embodiment, the therapy system 100 further comprises driving means 40 for rotating the X-Ray device 10 about the rotation axis 20, said driving means 40 being at least partially arranged outside of the nozzle 5. Several kinds of driving means can be used to that effect, such as for example hydraulic means or electric means such as an electric motor, operatively coupled to the cylindrical neck 30 for rotating the X-Ray device 10 about the rotation axis 20. An angle of rotation between the first and the second position is for example an angle of 30 degrees. Appropriate stops, such as for example adjustable screw stops, may be provided for ensuring an accurate positioning of the X-Ray device 10 in its first and/or second position. Other well known means may also be used for decoupling and/or switching off the driving means 40 when the X-Ray device 10 reached its first or second position.

As is well known, the X-ray source 12 must be fed with electrical power in order to emit X-rays and, in many cases, it must also be cooled with a cooling fluid.

Preferably, an electric power source for providing electric power to the X-Ray source 12 is arranged outside of the nozzle 5 and the electrical conductors 41 which connect said power source to the X-Ray source 12 are passing through the open side 31 of the cylindrical neck 30 of the container 14, as can be seen on FIG. 5. The same path may also be used by fluid ducts for bringing cooling fluid to and removing it from the X-Ray source 12. Hence, these components will also be able to operate at the external air pressure.

Advantageously, the rotation axis 20 of the X-Ray device 10 is substantially perpendicular to the central propagation axis 22 of the charged particle beam 6, as can be seen on FIG. 5. Since a nozzle 5 is generally oblong in the Z direction, such a configuration allows to have a relatively short rotation axle in comparison with a case in which the rotation axis 20 would be parallel to the central beam propagation axis 22.

Advantageously the nozzle 5 comprises a removable hollow lid 42 for receiving the X-Ray device 10 into the second position. Such a lid permits to have an easy access to the X-Ray device 10, for example for maintenance purposes.

The present invention has been described in terms of specific embodiments, which are illustrative of the invention and not to be construed as limiting. More generally, it will be appreciated by persons skilled in the art that the present invention is not limited by what has been particularly shown and/or described hereinabove. The invention resides in each and every novel characteristic feature and each and every combination of characteristic features.

Reference numerals in the claims do not limit their protective scope.

Use of the verbs "to comprise", "to include", "to be composed of", or any other variant, as well as their respective conjugations, does not exclude the presence of elements other than those stated.

Use of the article "a", "an" or "the" preceding an element does not exclude the presence of a plurality of such elements.

Summarized, the invention may also be described as follows: A therapy system 100 for irradiating a target volume 2 of a patient 1 with a charged particle beam 6, comprising a beam generator 3, a beam transport system 4, and a nozzle 5 for distributing the beam to the target volume 2, the nozzle 5 being, when in operation, under vacuum. The therapy system 100 comprises an X-Ray device 10 which is rotatably mounted inside the nozzle 5 between a first position and a second position. In the first position, an X-Ray source 12 within the X-Ray device 10 is able to emit X-Rays along a charged particle beam path for generating an X-Ray image on a corresponding X-Ray receiving device 11 arranged opposite to the patient 1, said X-Ray image serving to determine a correct position of the target volume 2 with regard to the charged particle beam 6. In the second position, the X-Ray device is set outside of a charged particle beam treatment path envelope 23, so that the charged particle beam 6 can reach and irradiate the target volume 2.

The invention claimed is:

1. Therapy system (100) for irradiating a target volume (2) within a patient (1) with a charged particle beam (6), comprising
   a charged particle beam generator (3),
   a beam transport system (4) for transporting the charged particle beam (6),
   a nozzle (5) for delivering the charged particle beam (6) to the target volume (2),
   an X-Ray device (10) comprising an X-Ray source (12) for emitting X-Rays towards the target volume (2), the X-Ray device (10) being movably mounted into the nozzle (5) between a first position wherein the X-Ray device (10) is inside of a treatment path envelope (23) of the charged particle beam (6) within the nozzle (5) and a second position wherein the X-Ray device (10) is outside of said treatment path envelope (23),
   an X-Ray receiving device (11) mounted opposite to the patient (1) with regard to the X-Ray source (12), and in optical alignment with the X-Ray source (12) when the X-Ray device (10) is in the first position,
   wherein the therapy system further comprises vacuum means (7) for creating a vacuum within the nozzle (5) so that, in operation, an internal air pressure inside the nozzle is lower than an external air pressure outside the nozzle, and the X-Ray device (10) is rotatably mounted into the nozzle between the first and the second position about a rotation axis (20).

2. Therapy system according to claim 1, wherein the X-Ray device (10) comprises a container (14) inside which the X-Ray source (12) is mounted, said container (14) having a cylindrical neck (30) whose axis is the rotation axis (20), said cylindrical neck (30) extending in an airtight manner through a circular opening of the nozzle (5) and emerging at an open side (31) of the neck at least partially outside of the nozzle (5) so that an inside of the container (14) is, in operation, at the external air pressure.

3. Therapy system according to claim 2, further comprises driving means (40) for rotating the X-Ray device (10) about the rotation axis (20), and the driving means (40) are at least partially arranged outside of the nozzle (5).

4. Therapy system according to claim 2, further comprising electrical conductors (41) for providing electrical power to the X-ray source (12), said electrical conductors (41) connecting the X-Ray source (12) to an electric power source arranged outside of the nozzle (5) and said electrical conductors 41 passing through the open side (31) of the cylindrical neck (30) of the container (14).

5. Therapy system according to claim 1, wherein the rotation axis (20) is substantially perpendicular to the central propagation axis (22) of the charged particle beam.

6. Therapy system according to claim 1, wherein the nozzle (5) further comprises a removable hollow lid (42) for receiving the X-Ray device (10) into the second position.

* * * * *